United States Patent [19]

Muschaweck et al.

[11] Patent Number: 4,564,625
[45] Date of Patent: Jan. 14, 1986

[54] BINARY COMPOSITIONS OF PENBUTOLOL AND FUROSEMIDE OR PIRETANIDE

[75] Inventors: Roman Muschaweck, Frankfurt am Main; Werner Fülberth, Kelkheim; Alfred Sickmüller, Frankfurt am Main, all of Fed. Rep. of Germany

[73] Assignee: Hoechst Aktiengesellschaft, Frankfurt am Main, Fed. Rep. of Germany

[21] Appl. No.: 608,915

[22] Filed: May 10, 1984

Related U.S. Application Data

[63] Continuation of Ser. No. 279,736, Jul. 2, 1981, abandoned.

[30] Foreign Application Priority Data

Jul. 4, 1980 [DE] Fed. Rep. of Germany ....... 3025367

[51] Int. Cl.$^4$ ........................................... A61K 31/135
[52] U.S. Cl. ................................ 514/429; 260/465 E; 514/471; 514/650; 548/577; 549/494; 564/338
[58] Field of Search ...................... 260/239.65, 465 E; 548/569; 564/338, 339; 424/285, 274; 514/471

[56] References Cited

U.S. PATENT DOCUMENTS

| | | | |
|---|---|---|---|
| 3,839,321 | 10/1974 | Weinstock | 424/229 X |
| 4,118,587 | 10/1978 | Coffen | 560/251 |
| 4,139,633 | 2/1979 | Brunner | 424/274 |
| 4,191,765 | 3/1980 | Fritsch et al. | 424/274 X |

FOREIGN PATENT DOCUMENTS

| | | |
|---|---|---|
| 356095 | 4/1980 | Austria . |
| 2227423 | 12/1972 | Fed. Rep. of Germany . |
| 2638716 | 3/1978 | Fed. Rep. of Germany . |

OTHER PUBLICATIONS

Bormann, et al., C.A., 84, 43,666y (1976).
Bormann, et al., C.A., 85, 123,756p (1976).
Merkel, et al., C.A., 86, 115,112f (1977).
Boissier, et al., C.A., 80, 66,731x (1974).
Hansson, et al., C.A., 85, 186,790r (1976).

*Primary Examiner*—Joseph Paul Brust
*Attorney, Agent, or Firm*—Curtis, Morris & Safford

[57] ABSTRACT

Salts formed between penbutolol and furosemide or piretanide, pharmaceutical compositions containing such salts, and methods for treating diseases of the coronary and circulatory systems with such salts.

4 Claims, No Drawings

BINARY COMPOSITIONS OF PENBUTOLOL AND FUROSEMIDE OR PIRETANIDE

This is a continuation application of Ser. No. 279,736 filed July 2, 1981 and now abandoned.

The present invention related to salts formed between furos emide or piretanide as the acid component and penbutolol or (-)-3-[4-[3-(3,4-dimethoxyphenylethylamino)-2-hydroxypropoxy]-phenyl]-crotononitrile as the base component, and a process for their preparation, and also a composition containing at least two of the following components:

(A) furosemide or piretanide, (B) penbutolol or (-)-3-[4-[3-(3,4-dimethoxyphenylethylamino)-2-hydroxypropoxy]-phenyl]-crotononitrile, and (C) an abovementioned salt, and the use of this composition for the treatment of diseases of the coronary and circulatory system.

Coronary circulation diseases constitute a considerable risk factor in life expectancy. In particular, the treatment of high blood pressure is therefore an essential requirement.

It is known that high blood pressure can be treated both with diuretics and with β-blockers.

Both compounds of the "low-ceiling" diuretic type and compounds of the "high-ceiling" diuretic type are applied in the treatment of high blood pressure with diuretics. A high-ceiling diuretic is understood as meaning a diuretic with a rapid onset of the action, a strong action and an early subsidence of the action. A low-ceiling diuretic is a diuretic with a slow onset of the action and a sustained action. A diuretic influences high pressure essentially by increasing the excretion of water and sodium ions, which causes a reduction in the volumetric load on the circulation.

In contrast, the use of a β-blocker causes a reduction in the blood pressure, frequently only after a relatively long period of treatment, and this reduction proceeds by another, hitherto unexplained mechanism.

A number of combinations of diuretics with β-blockers for the treatment of high blood pressure are known, in which different reciprocal actions are observed between the components of the combinations. In some cases, the action is made up of the sum of those of the two individual components, and in other cases, more or less substantial impairment of the action occurs, up to inactivity.

Examples of known combinations are as follows:
pindolol and hydrochlorothiazide (Med. J. Aust. 1/18, 650-653 (1976)),
timolol and bendrofluazide (Clin. Trials J. 14/5, 173-180 (1977)),
timolol maleate and bendrofluazide (J. Int. Med. Res. 5/2, 114-119 (1977)),
pindolol and hydrotrichlorothiazide (Z. Kardiol. 66/9, 508-510 (1977)),
atenolol and chlorthalidone (Brit. Med. J. 1/6053, 76-78 (1977)),
oxprenolol and chlorthalidone (Bol. Soc. Port. Kardiol. 15/3, 147-169 (1977)),
propranolol and chlorthalidone (Hell. Cardiol. Rev. 18/2, 162-166 (1977)),
oxprenolol and chlorthalidone (Invest. Med. Int. 5/2, 119-126 (1978)),
oxprenolol and chlorthalidone (Verh. dtsch. Ges. Inn. Med. 83, 325-327 (1977)).

The subject of the invention is a new combination of a diuretic and a β-blocker, which is distinguished by special properties.

The combination contains furosemide or piretanide as the diuretic component and penbutolol or (-)-3-[4-[3-(3,4-dimethoxyphenylethylamino)-2-hydroxypropoxy]-phenyl]-crotononitrile as the β-blocker component. For the sake of simplicity, the last-mentioned compound is designated as "Hoe 224" in the following text.

The said compounds are known compounds.

Furosemide is 4-chloro-2-[(2-furanoylmethyl)-amino]-5-sulfamoyl-benzoic acid of the formula I

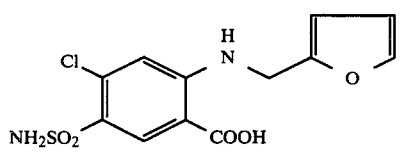

Piretanide is 4-phenoxy-3-(1-pyrrolidinyl)-5-sulfamoylbenzoic acid, which has the formula II

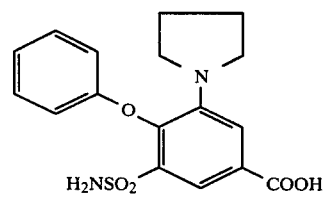

Penbutolol is (S)-(-)-(1-tert.-butylamino)-3-(2-cyclopentylphenoxy)-2-propanol of the formula III

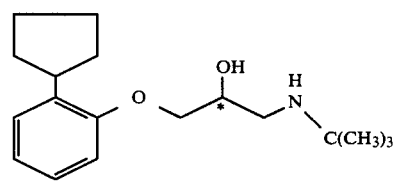

(-)-3-[4-[3-(3,4-Dimethoxyphenylethylamino)-2-hydroxypropoxy]-phenyl]-crotononitrile (Hoe 224) has the formula IV

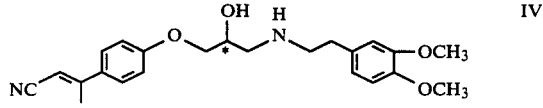

In their capacity as carboxylic acids, the diuretics used according to the invention are capable of forming salts with basic compounds. In contrast, the β-blockers used according to the invention have basic properties. Accordingly, they can form salts with acid compounds and can also react with the diuretics to form salts. A reaction of this type results in new compounds which have the character of salts and which combine the pharmacological action of the acid and basic components.

The formation of salts can already take place to a certain extent on bringing together, and especially on compressing, the dry components. This can be achieved specifically by bringing together solutions, especially aqueous or alcoholic solutions, of the diuretic on the one hand and of the β-blocker on the other hand, and crystallizing the salt from these solutions.

Both the salt of equimolar amounts of the diuretic and the β-blocker, and mixtures of the two components or of the salt with one or other component, which mixtures can also contain one or other component in excess, are suitable for use as a pharmaceutical preparation. The ratio of diuretic to β-blocker can be varied in use, depending on the condition of the patient.

Accordingly, the subject of the invention is a salt formed between furosemide or piretanide as the acid component and penbutolol or Hoe 224 as the base component.

A further subject of the invention is a process for the preparation of a salt of this type, which comprises bringing together furosemide or piretanide on the one hand and penbutolol or Hoe 224 on the other hand, preferably in the form of solutions. A further subject of the invention is a composition which contains at least two of the following components (A) furosemide or piretanide, (B) penbutolol or Hoe 224 and (C) a salt of one of each of components (A) and (B), and the use of a composition of this type for the treatment of diseases of the coronary and circulatory system.

It is known that β-blockers frequently possess properties for inhibiting saluresis and diuresis. Examinations carried out to this effect by the present applicants' assignee have shown, for example, a dose-dependent reduction in the extent of excretion both of urine and of sodium, potassium and chlorine ions under the action of pindolol. This excretion-inhibiting effect cannot easily be overcome using diuretics. Thus, for example, hydrochlorothiazide can scarcely overcome the diuresis-inhibiting action of pindolol, even in maximum doses (1 to 2 mg/kg), let alone cause a total excretion corresponding to the preparation. The same applies to the action of furosemide when pindolol is administered at the same time.

However, there are also β-blockers which do not exhibit an inhibition of diuresis and saluresis in normal experimental animals. These β-blockers include, for example, penbutolol. The saluretic activity of thiazides, for example of hydrochlorothiazide, is not influenced by this compound when administered orally in doses of 5 to 50 mg/kg. It was surprising, on the other hand, that penbutolol exerts a significant influence on the salidiuresis of furosemide. The excretion values after furosemide are reduced in the first 5 hours by the simultaneous administration of penbutolol (5 or 50 mg/kg, administered orally), but this is then followed by an extensive compensation of this excretion deficit in the following hours, especially in the 6th to 24th hour after oral administration of the two compounds. This action is shown in a particularly impressive way by comparing the treatment using furosemide by itself with a treatment using furosemide and penbutolol. A comparison of this type is shown in the following table. It can be seen that, on simultaneous administration of penbutolol and furosemide, excretion is reduced in the first 5 hours and increased in the following hours up to the 24th hour, compared with excretion after administration of furosemide by itself. The end values of the two series of experiments are essentially the same. Similar observations were made for combinations with the other diuretics and β-blockers to be used according to the invention.

The surprising effect of a delay in the salidiuretic action of furosemide by simultaneous administration of penbutolol is very desirable for the treatment of high blood pressure, because a milder diuresis and saluresis sustained over a relatively long time is as a rule considered to be advantageous for the patient. A new principle of action has been found with the combination according to the invention, which makes it possible to use certain high-ceiling diuretics in such a way that they have the action of a low-ceiling diuretic in the patient.

The doses to be used can be individually different and can vary depending on the nature of the condition to be treated. They are 1 to 100 mg/dose for each component of the combination, or twice the amount for one of the salts according to the invention. The ratio of the components can be varied as desired. Combinations of the β-blocker and the diuretic in a ratio of 1:4 to 10:1 have proved particularly advantageous: a ratio β-blocker:diuretic of 2:1 to 10:1 being particularly important. The figures indicated relate to weight ratios. A mixture of 20 mg of furosemide and 40 mg of penbutolol per dose, or a mixture of 3 to 12 mg of piretanide and 40 mg of penbutolol per dose, for example, is particularly important.

The active ingredients can not only be used as the free acid or base or as a salt of the acid diuretic and the basic β-blocker, but it is also possible to use other salts of the individual components. Examples of such salts are the alkali metal salts of the acid diuretics or their salts with organic bases such as glucosamines, trishydroxy-ethylamine, ethanolamine, benzylamine or diethylamine, and the salts of the β-blockers with mineral acids or their salts with organic acids such as maleic acid, fumaric acid, mucic acid, tartaric acid, glycolic acid, pyruvic acid, malic acid, formic acid, salicylic acid and aminosalicylic acid. There is the restriction that the salt-forming base component or acid component must be physiologically acceptable.

If desired, the compositions according to the invention can be present together with suitable pharmaceutical adjuncts in galenic preparations suitable for oral, intravenous or intramuscular administration, and these preparations can also be combined with compositions for the delayed release of the active ingredient. Examples of preparations of this type are tablets, coated tablets, capsules or solutions. Any pharmaceutically conventional adjuncts can be used to make up the preparations.

The active ingredients can be mixed and formulated with the adjuncts in the conventional manner. If desired, for the purpose of retardation, solid medicaments or their intermediates can be covered with a porous insoluble film. The following examples are intended to illustrate the invention in greater detail without in any way limiting it.

TABLE

Salidiuresis in rats on oral administration of furosemide or furosemide and penbutolol (1:2 parts by weight)

| Dose* mg/kg | Period of measurement | Urine (ml/kg) | | $Na^+$ (mmoles/kg) | |
|---|---|---|---|---|---|
| | | Furosemide | Furosemide and penbutolol | Furosemide | Furosemide and penbutolol |
| 8 | 1st–5th hour | 17.0 | 10.7 | 0.66 | 0.35 |

TABLE-continued

Salidiuresis in rats on oral administration of furosemide or furosemide and penbutolol (1:2 parts by weight)

| Dose* mg/kg | Period of measurement | Urine (ml/kg) Furosemide | Urine (ml/kg) Furosemide and penbutolol | Na+ (mmoles/kg) Furosemide | Na+ (mmoles/kg) Furosemide and penbutolol |
|---|---|---|---|---|---|
| 8 | 6th–24th hour | 17.6 | 34.5 | 1.27 | 3.39 |
| 8 | 1st–24th hour | 34.6 | 45.2 | 1.93 | 3.74 |
| 16 | 1st–5th hour | 39.3 | 24.0 | 3.19 | 1.37 |
| 16 | 6th–24th hour | 13.2 | 40.9 | 1.09 | 3.39 |
| 16 | 1st–24th hour | 52.5 | 64.9 | 4.28 | 4.76 |
| 32 | 1st–5th hour | 62.5 | 34.3 | 6.08 | 2.88 |
| 32 | 6th–24th hour | 13.6 | 39.7 | 1.10 | 3.97 |
| 32 | 1st–24th hour | 76.1 | 74.0 | 7.18 | 6.85 |
| 128 | 1st–5th hour | 83.5 | 22.8 | 8.63 | 1.86 |
| 128 | 6th–24th hour | 27.2 | 76.5 | 2.19 | 8.08 |
| 128 | 1st–24th hour | 110.7 | 99.3 | 10.82 | 9.94 |

*The figures represent the dose of furosemide. If penbutolol was also administered, its dose was double this amount.

EXAMPLES

Example 1

Capsules containing a combination of furosemide in the form of pellets and penbutolol sulfate in the form of tablets:

| Furosemide pellets | |
|---|---|
| 1. Furosemide | 30 mg |
| 2. Pellet base | 100 mg |
| (a) sucrose | (70 mg) |
| (b) corn starch | (30 mg) |
| 3. Polyvinylpyrrolidone K 25 | 2 mg |
| 4. Talc | 10 mg |
| 5. Shellac | 1 mg |
| 6. Stearic acid | 2 mg |
| | 145 mg |

In a suitable coating drum, a 10% strength solution of (3) in ethanol is applied to the pellet base (2) and a mixture of (1) and (4) is then sprinkled in.

The pellets consisting of (1) to (4) are coated with a 10% strength solution of (5) and (6) in a mixture of ethyl acetate/ethanol.

| Penbutolol tablets | |
|---|---|
| 1. Penbutolol sulfate | 40 mg |
| 2. Corn starch | 14 mg |
| 3. Talc | 3 mg |
| 4. Highly disperse silicon dioxide | 2 mg |
| 5. Magnesium stearate | 1 mg |
| | 60 mg |

The tablet mixture consisting of substances (1) to (5) is converted to granules and these are compressed to biconvex tablets.

Furosemide pellets corresponding to a content of 30 mg of furosemide, and in each case 1 penbutolol tablet containing 40 mg, are filled into hard gelatin capsules.

Example 2

Tablets containing a combination of furosemide and penbutolol sulfate:

| | | |
|---|---|---|
| 1. Furosemide | | 20 mg |
| 2. Penbutolol sulfate | | 40 mg |
| 3. Lactose | | 80 mg |
| 4. Corn starch | | 46 mg |
| 5. Polyvinylpyrrolidone K 25 | | 5 mg |
| 6. Highly disperse silicon dioxide | | 4 mg |
| 7. Talc | | 4 mg |
| 8. Magnesium stearate | | 1 mg |
| | | 200 mg |

The tablet mixture of substances (1) to (8) is converted to granules and these are compressed to biconvex tablets.

Film tablets

The tablets are coated with one of the conventional film lacquers.

Example 3

Capsules containing a combination of piretanide in the form of pellets and penbutolol sulfate in the form of tablets:

| Piretanide pellets | |
|---|---|
| 1. Piretanide | 6.00 mg |
| 2. Pellet base | 140.00 mg |
| (a) sucrose | (100.00 mg) |
| (b) corn starch | (40.00 mg) |
| 3. Polyvinylpyrrolidone K 25 | 1.00 mg |
| 4. Shellac | 2.25 mg |
| 5. Stearic acid | 4.50 mg |
| | 153.75 mg |

In a suitable coating drum, an aqueous suspension of (1) and (3) is sprayed onto the pellet base (2).

After drying, the pellets consisting of (1) to (3) are coated with a 10% strength solution of (4) and (5) in a mixture of ethyl acetate/ethanol.

Piretanide pellets corresponding to a content of 6 mg of piretanide, and in each case 1 penbutolol tablet containing 40 mg (see Example 1), are filled into hard gelain capsules.

Example 4

Tablets containing a combination of piretanide and penbutolol sulfate:

| | |
|---|---|
| 1. Piretanide | 6 mg |
| 2. Penbutolol sulfate | 40 mg |
| 3. Microcrystalline cellulose | 104 mg |
| 4. Corn starch | 43 mg |
| 5. Polyvinylpyrrolidone | 6 mg |
| 6. Magnesium stearate | 1 mg |

-continued

|  |
|---|
| 200 mg |

The tablet mixture of substances (1) to (6) is converted to granules and these are compressed to biconvex tablets.

Film tablets

The tablets are coated with one of the conventional film lacquers.

Example 5

Capsules containing a combination of furosemide in the form of pellets and preparation Hoe 224 in the form of tablets:

| Tablets of preparation Hoe 224 | |
|---|---|
| 1. Preparation Hoe 224 | 50 mg |
| 2. Corn starch | 9 mg |
| 3. Talc | 3 mg |
| 4. Highly disperse silicon dioxide | 2 mg |
| 5. Magnesium stearate | 1 mg |
| | 65 mg |

The tablet mixture consisting of substances (1) to (5) is converted to granules and these are compressed to biconvex tablets.

To make up the preparation of the combination, furosemide pellets corresponding to a content of 30 mg of furosemide (see Example 1), and in each case 1 tablet containing 50 mg of Hoe 224, are filled into hard gelatin capsules.

Example 6

Tablets containing a combination of furosemide and preparation Hoe 224:

| 1. Furosemide | 20 mg |
|---|---|
| 2. Preparation Hoe 224 | 100 mg |
| 3. Lactose | 110 mg |
| 4. Corn starch | 60 mg |
| 5. Talc | 20 mg |
| 6. Highly disperse silicon dioxide | 8 mg |
| 7. Magnesium stearate | 2 mg |
| | 320 mg |

The tablet mixture of substances (1) to (7) is converted to granules and these are compressed to biconvex tablets.

Film tablets

The tablets are coated with one of the conventional film lacquers.

Example 7

Capsules containing a combination of piretanide in the form of pellets and preparation Hoe 224 in the form of tablets:

Piretanide pellets corresponding to a content of 6 mg of piretanide (see Example 3), and one tablet containing 50 mg of preparation Hoe 224 (see Example 5), are filled into hard gelatin capsules.

Example 8

Tablets containing a combination of piretanide and preparation Hoe 224:

| 1. Piretanide | 6 mg |
|---|---|
| 2. Preparation Hoe 224 | 60 mg |
| 3. Microcrystalline cellulose | 110 mg |
| 4. Corn starch | 47 mg |
| 5. Polyvinylpyrrolidone | 6 mg |
| 6. Magnesium stearate | 1 mg |
| | 230 mg |

The tablet mixture of substances (1) to (6) is converted to granules and these are compressed to biconvex tablets.

Film tablets

The tablets are coated with one of the conventional film lacquers.

Example 9

Preparation of a salt of penbutolol and furosemide:

0.1 mole (29 g) of penbutolol base is dissolved in 300 ml of ethanol and the solution is treated with a solution of 0.1 mole (33 g) of furosemide in 300 ml of acetone, while stirring. The crystal mass which slowly separates out after the addition of petroleum ether is filtered off with suction, washed thoroughly with an ether/petroleum ether mixture (1:1) and dried. Yield: quantitative.

Melting point: decomposition at a temperature of 93°–95° C.

We claim:

1. A composition comprising the two components
   (a) furosemide or piretanide and
   (b) penbutolol,
in a ratio by weight of (a):(b) of 1:2.

2. A composition comprising the two components
   (a) furosemide or piretanide and
   (b) penbutolol
in pharmaceutical dosage unit form, wherein each dosage unit comprises a mixture of 3 mg of 12 mg of piretanide and 40 mg of penbutolol.

3. A composition as in claim 1 in pharmaceutical dosage unit form wherein each dosage unit comprises a mixture of 20 mg of furosemide and 40 mg of penbutolol.

4. A method for treating diseases of the coronary and circulatory systems in a patient suffering therefrom, which method comprises administering to said patient a therapeutically effective amount of a composition as in claim 1.

* * * * *